(12) United States Patent
Ladebeck et al.

(10) Patent No.: US 7,835,781 B2
(45) Date of Patent: Nov. 16, 2010

(54) DEVICE FOR SUPERPOSED MRI AND PET IMAGING

(75) Inventors: Ralf Ladebeck, Erlangen (DE); Diana Martin, Herzogenaurach (DE); Norbert Rietsch, Dormitz (DE)

(73) Assignee: Siemens Aktiengesellschaft, Munich (DE)

( * ) Notice: Subject to any disclaimer, the term of this patent is extended or adjusted under 35 U.S.C. 154(b) by 636 days.

(21) Appl. No.: 11/882,693

(22) Filed: Aug. 3, 2007

(65) Prior Publication Data

US 2008/0033279 A1    Feb. 7, 2008

(30) Foreign Application Priority Data

Aug. 4, 2006    (DE) .................. 10 2006 036 572

(51) Int. Cl.
*A61B 5/05*    (2006.01)
*A61B 6/00*    (2006.01)
(52) U.S. Cl. ...................................... 600/411; 600/436

(58) Field of Classification Search .................. 600/407, 600/411, 436
See application file for complete search history.

(56) References Cited

U.S. PATENT DOCUMENTS

2004/0097800 A1    5/2004    Crosetto

FOREIGN PATENT DOCUMENTS

WO    WO 2006/071922 A2    7/2006

*Primary Examiner*—Eric F Winakur
*Assistant Examiner*—Michael T Rozanski
(74) *Attorney, Agent, or Firm*—Harness, Dickey & Pierce, P.L.C.

(57) ABSTRACT

A device is disclosed for superposed MRI and PET imaging and includes an MRI tube that has a first field of view along its longitudinal direction, and a multiplicity of PET detection units arranged opposite one another in pairs about the longitudinal direction. In at least one embodiment the many PET detection units define a second field of view along the longitudinal direction, and their arrangement density along the longitudinal direction is optimized such that the second field of view substantially corresponds to the first field of view.

3 Claims, 3 Drawing Sheets

DEVICE FOR SUPERPOSED MRI AND PET IMAGING

PRIORITY STATEMENT

The present application hereby claims priority under 35 U.S.C. §119 on German patent application number DE 10 2006 036 572.0 filed Aug. 4, 2006, the entire contents of which is hereby incorporated herein by reference.

FIELD

Embodiments of the present invention generally relate to a device for superposed MRI and PET imaging.

BACKGROUND

Alongside magnetic resonance tomography (MRI) positron emission tomography (PET) has also become increasingly widespread of recent years in medical diagnosis. While MRI is an imaging method for displaying structures and slice images in the interior of the body, PET enables a visualization and quantification of metabolic activities in vivo.

PET uses the particular properties of positron emitters and positron annihilation in order to determine the function of organs or cell areas quantitively. In this case, before the examination the patient is administered appropriate radiopharmaceuticals that are marked with radionuclides. In the event of decay, the radionuclides emit positrons that interact with an electron after a short distance, resulting a so-called annihilation. Two gamma quanta are produced in this case and fly apart from one another in opposite directions (offset by 180°). The gamma quanta are detected by two opposite PET detector modules inside a specific time window (coincidence measurement), as a result of which the location of the annihilation is determined at a position on the connecting line between these two detector modules.

For detection, in the case of PET the detector module must generally cover a major part of the length of the gantry arc. The module is subdivided into detector elements with a side length of a few millimeters. When detecting a gamma quantum, each detector element generates an event record that specifies the time and the detection location, that is to say the appropriate detector element. These items of information are transferred to a fast logic unit and compared. If two events coincide with a maximum time spacing, it is assumed there is a gamma decay process on the connecting line between the two associated detector elements. The reconstruction of the PET image is performed with the aid of a tomography algorithm, that is to say the so-called back projection.

A superposed imaging of the two methods is desirable in many instances on the basis of the different items of information that are obtained by MRI and PET.

For future systems, an attempt is currently being made to combine the MRI and PET imaging methods in one unit, and to make it possible to use them simultaneously, as far as possible. An avalanche photodiode array (APD photodiode array) with an upstream array of lutetium oxyorthosilicate crystals (LSO crystals) is favored in this case as a PET detector module. FIG. 5 shows a schematic of a perspective view of the structure of a conventional PET detection module in accordance with the prior art. The PET detector module comprises an APD photodiode array 5 with an upstream array of LSO crystals 4. An electrical amplifier circuit (AMP) 6 is arranged in the axial direction of the PET detection module, that is to say downstream of the APD photodiode array 5.

Because of the crystals, the PET detector module is a relatively expensive component. Cost effective approaches would be advantageous for mass production.

Another proposal uses a gantry in whose z-direction (longitudinal direction) and circumferential direction an extended array of APD/LSO detectors is arranged. Seated in a base arrangement inside the PET detector is an MRI antenna that is separated from the detector for the purpose of mutual interference decoupling by a PET-transparent, MRI-compatible RF shield.

An MRI unit usually has a field of view (FOV) approximately 50 cm long in the longitudinal direction (z-direction). A PET system usually has a field of view (FOV) only approximately 15 cm long in the z-direction. In order to reduce costs for mass production, it is possible to utilize the fact that the MRI examination generally lasts much longer than the PET data acquisition. It is thereby possible to take PET pictures sequentially over time by displacing the detector module. When the MRI unit has a field of view approximately 50 cm long in the z-direction, and the PET system has a field of view approximately 15 cm long in the z-direction, it would then be necessary to displace the PET system 3 to 4 times in order to cover the field of view of the MRI unit. The disadvantage of this method is that there is a need for mechanical movement.

WO 2006/071922 A2 discloses a device for superposed magnetic resonance tomography and positron emission tomography imaging that exhibits a magnetic resonance tomography tube and a multiplicity of positron emission tomography detection units arranged opposite one another in pairs about the longitudinal direction of the magnetic resonance tomography tube.

SUMMARY

In at least one embodiment, the present invention provides a device for superposed MRI and PET imaging that, on the one hand, can be produced at a moderate price and, on the other hand, does not carry out a relative movement between the PET system and the MRI unit.

According to at least one embodiment of the invention, an arrangement density of the PET detection units along the longitudinal direction is optimized such that the second field of view is substantially the same as the first field of view. This advantageously optimizes the number of PET detection units such that the costs for the PET detection units are reduced and there is no need for relative movement between the PET system and the MRI unit.

BRIEF DESCRIPTION OF THE DRAWINGS

Preferred example embodiments of the invention will now be described with reference to the attached drawings, in which.

Figure 1:
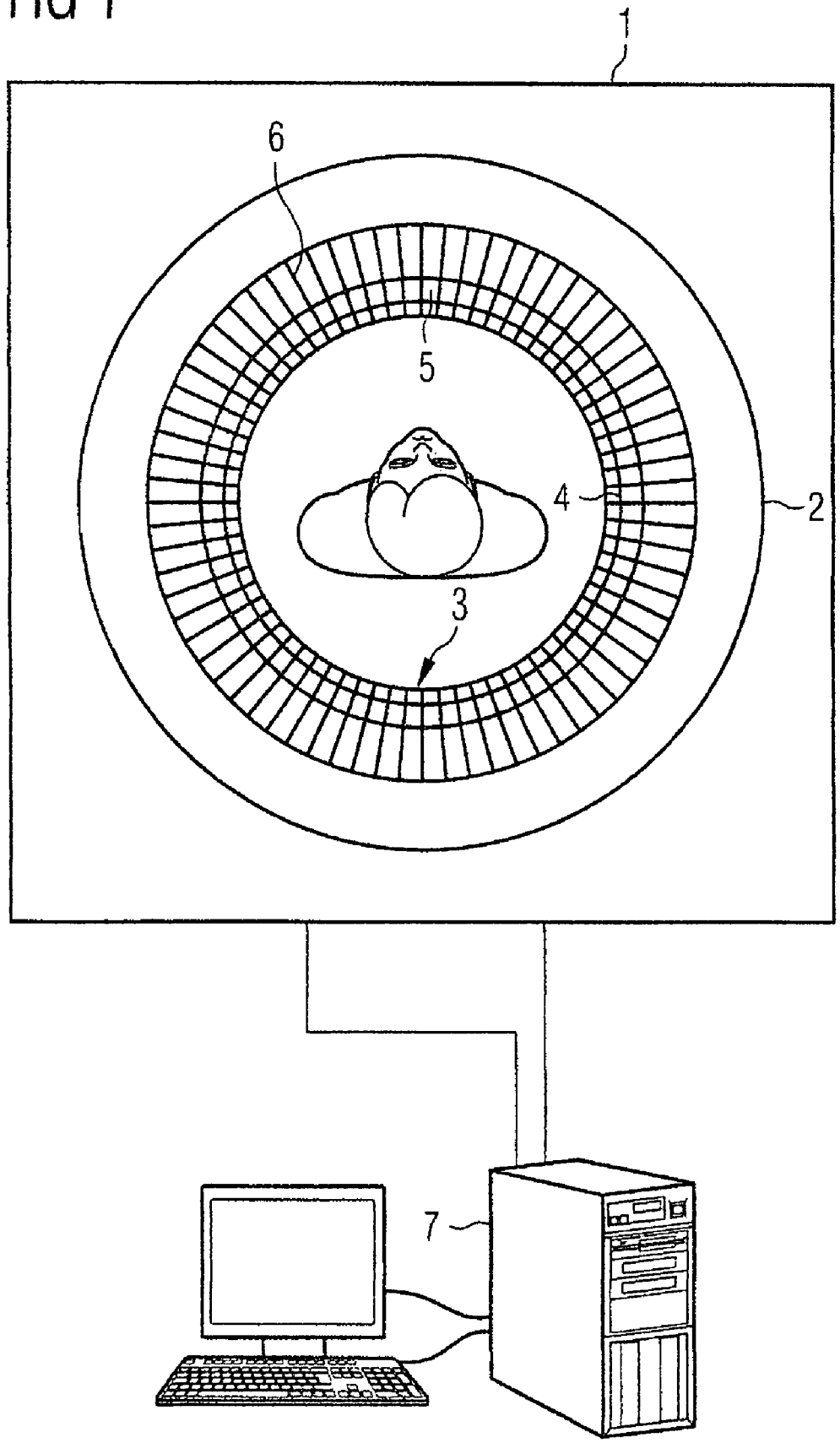
FIG. 1 shows a device for superposed MRI and PET imaging in accordance with an embodiment of the present invention.

The example embodiments of the present invention are described below with reference to the drawings.

DETAILED DESCRIPTION OF THE EXAMPLE EMBODIMENTS

The terminology used herein is for the purpose of describing particular embodiments only and is not intended to be limiting of the present invention. As used herein, the singular forms "a", "an", and "the" are intended to include the plural forms as well, unless the context clearly indicates otherwise. It will be further understood that the terms "includes" and/or "including", when used in this specification, specify the presence of stated features, integers, steps, operations, elements, and/or components, but do not preclude the presence or addition of one or more other features, integers, steps, operations, elements, components, and/or groups thereof.

Spatially relative terms, such as "beneath", "below", "lower", "above", "upper", and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if the device in the figures is turned over, elements described as "below" or "beneath" other elements or features would then be oriented "above" the other elements or features. Thus, term such as "below" can encompass both an orientation of above and below. The device may be otherwise oriented (rotated 90 degrees or at other orientations) and the spatially relative descriptors used herein are interpreted accordingly.

Although the terms first, second, etc. may be used herein to describe various elements, components, regions, layers and/or sections, it should be understood that these elements, components, regions, layers and/or sections should not be limited by these terms. These terms are used only to distinguish one element, component, region, layer, or section from another region, layer, or section. Thus, a first element, component, region, layer, or section discussed below could be termed a second element, component, region, layer, or section without departing from the teachings of the present invention.

In describing example embodiments illustrated in the drawings, specific terminology is employed for the sake of clarity. However, the disclosure of this patent specification is not intended to be limited to the specific terminology so selected and it is to be understood that each specific element includes all technical equivalents that operate in a similar manner.

Referencing the drawings, wherein like reference numerals designate identical or corresponding parts throughout the several views, example embodiments of the present patent application are hereafter described. Like numbers refer to like elements throughout. As used herein, the terms "and/or" and "at least one of" include any and all combinations of one or more of the associated listed items.

Figure 2:
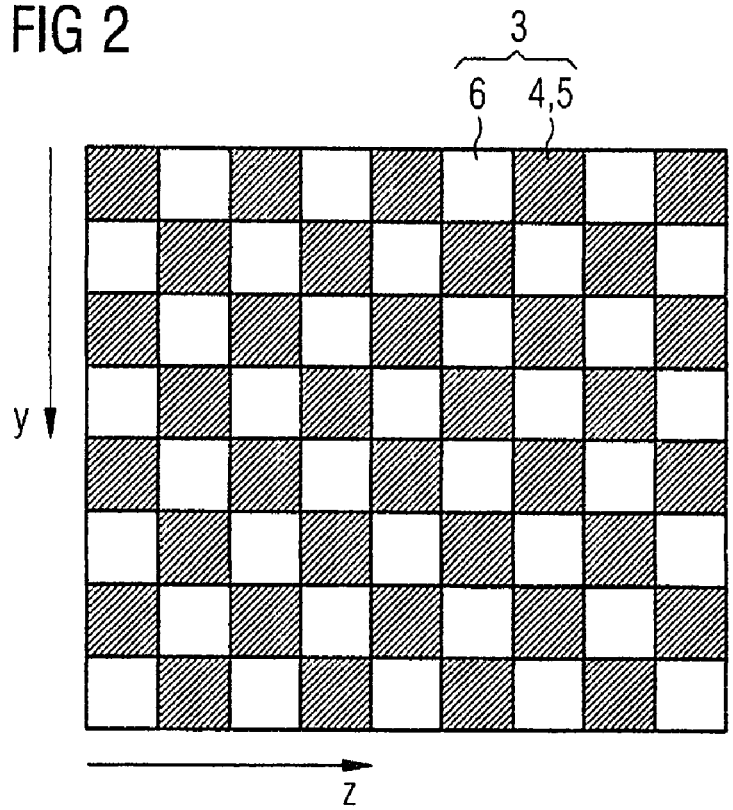
FIG. 2 shows an arrangement of PET detection units in a device for superposed MRI and PET imaging in accordance with a first example embodiment of the present invention.
Figure 3:
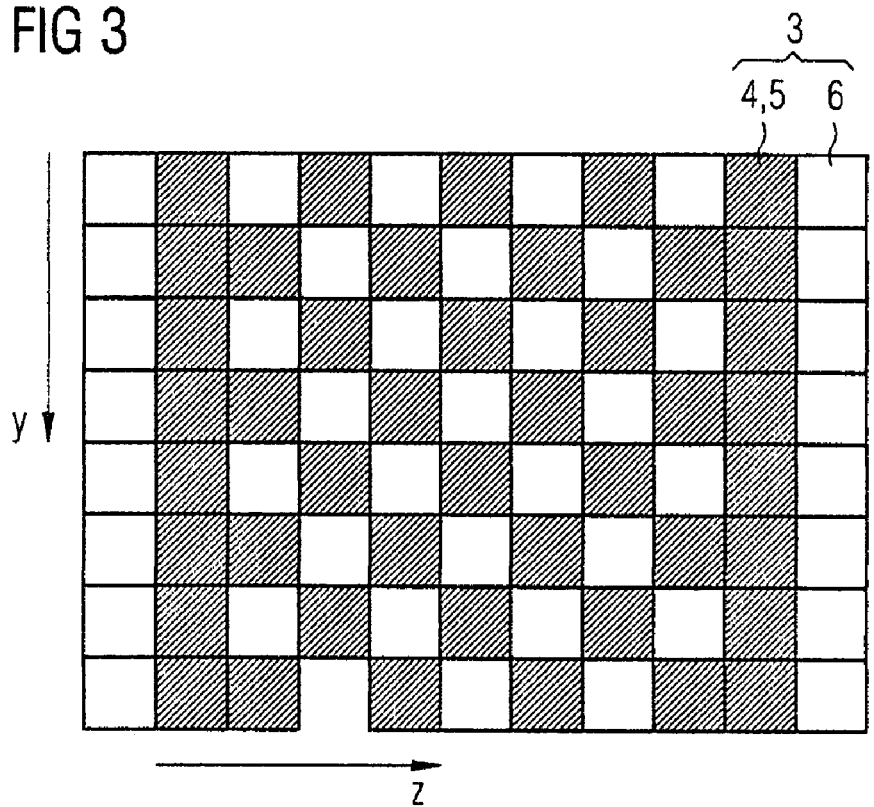
FIG. 3 shows an arrangement of PET detection units in a device for superposed MRI and PET imaging in accordance with a second example embodiment of the present invention.
Figure 4:
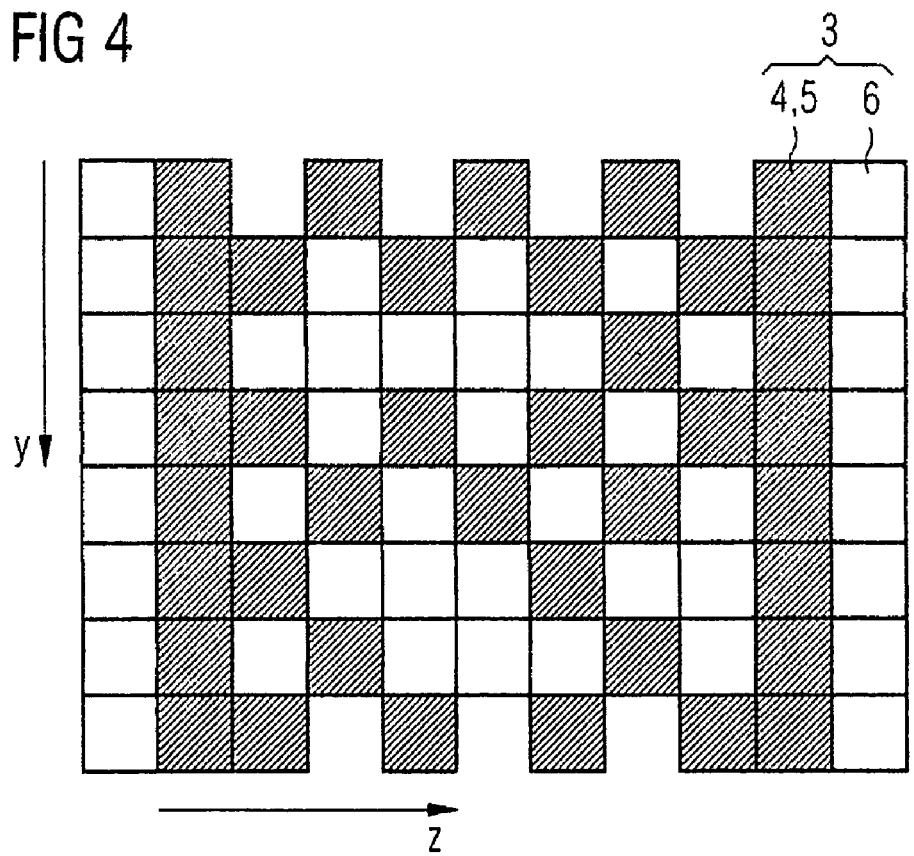
FIG. 4 shows an arrangement of PET detection units in a device for superposed MRI and PET imaging in accordance with a third example embodiment of the present invention.
Figure 5:
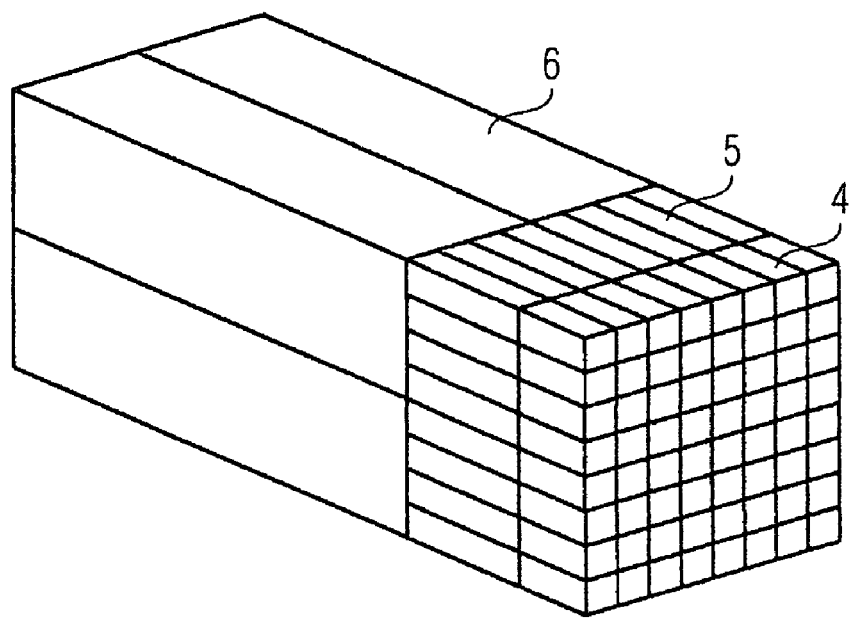
FIG. 5 shows a schematic of a perspective view of the structure of a conventional PET detection module in accordance with the prior art.

FIG. 1 shows a device 1 for superposed MRI and PET imaging in accordance with an embodiment of the present invention. The device 1 includes a known MRI tube 2. The MRI tube 2 defines a longitudinal direction z that extends orthogonally to the plane of the drawing of FIG. 1, and is shown in FIGS. 2 to 4. The y-direction shown in FIGS. 2 to 4 corresponds to a developed circumferential direction of the MRI tube 2.

As is shown in FIG. 1, a number of PET detection units 3 arranged opposite one another in pairs about the longitudinal direction z are arranged coaxially inside the MRI tube 2. The PET detection units 3 preferably comprise an APD photodiode array 5 with an upstream array of LSO crystals 4 and an electrical amplifier circuit (AMP) 6. However, at least one embodiment of the invention is not restricted to the PET detection units 3 with the APD photodiode array 5 and the upstream array of LSO crystals 4, but it is also more or less possible to use photodiodes, crystals and devices of other types for the purpose of detection.

A computer 7 is used to process the images for superposed MRI and PET imaging.

The MRI tube 2 defines a cylindrical, first field of view along its longitudinal direction z. The multiplicity of PET detection units 3 define a cylindrical, second field of view along the longitudinal direction z. According to the invention, the second field of view of the PET detection units 3 substantially corresponds to the first field of view of the MRI tube 2. This is implemented by an appropriate adaptation of the arrangement density of the PET detection units 3 along the longitudinal direction z.

FIG. 2 shows such an arrangement of the PET detection units 3, as well as the structure of the PET detection units 3 in accordance with a first example embodiment of the present invention.

A spacing is present between two neighboring APD photodiode arrays 5 with the respectively upstream arrays of LSO crystals 4, the result being to produce a chessboard-like pattern.

Moreover, it becomes clear here that the AMPs 6 are respectively not arranged in the radial direction of the PET detection unit 3, but in a plane parallel to the longitudinal direction z next to the associated LSO crystals 4 and APD photodiodes 5. The AMPs 6 are thus arranged next to the associated LSO crystals 4 and APD photodiodes 5 so that each PET detection unit 3 occupies a smaller space in the radial direction of the gantry.

In the case of the first example embodiment, both the first field of view and the second field of view can have, for example, a length of 50 cm in the z-direction.

The arrangement of the PET detection units 3 that is shown in FIG. 2 in the device for superposed MRI and PET imaging in accordance with the first example embodiment is based on the following considerations.

Were the second field of view defined in a classical way by homogeneous occupancy of the entire gantry with PET detection units 3, then the so-called 3D technique (for example "Theory and Practice of 3D PET, B. Bendriem, D. Townsend") yields a sensitivity distribution that is substantially higher at the center than at the edge of the second field of view. Moreover, this increased sensitivity would once again shorten the PET measuring time. However, this increased sensitivity is not necessary, since the patient must continue to remain lying at this position for measurement purposes because of the requirements of MRI.

The aim is to design the PET system such that although a field of view identical to the MRI tube 2 is considered (measuring sequence), the measuring time is also identical.

It is therefore possible to build the PET system with a reduced sensitivity. It is advantageous when the sensitivity is reduced at the center, in particular, since the highest sensitivity is present here in any case owing to the previously mentioned 3D technique.

It would be a conceivable possibility to use shorter crystals at the center of the PET system. This would save costs significantly, since the crystals are very expensive. A further conceivable possibility would be to omit entire crystals at the center of the PET system and to recover the information then lacking by interpolation. One approach to this end is to omit each second crystal. This is not very cost-efficient, since the costs for the AMPs 6 etc. accrue per PET detection unit 3, nevertheless.

It is to be preferred to omit at least each second PET detection unit 3 at the center of the PET system. This leads to a significantly higher saving in costs and offers, in addition, the possibility of fitting the required AMPs 6 (preamplifier and line driver) next to the associated PET detection unit 3. This saves space in the radial direction of the gantry, which is extremely expensive in an MRI system. This solution is shown in FIG. 2.

FIG. 3 shows a further arrangement of PET detection units 3 in a device for superposed MRI and PET imaging in accordance with a second example embodiment of the present invention.

The second example embodiment is modified with regard to the first example embodiment to the effect that the PET detection units 3 are respectively oriented at the end of the second field of view in the z-direction such that the LSO crystal array 4 and the APD photodiode array 5 are oriented toward the middle of the MRI tube 2, and the associated AMP 6 is oriented toward the edge of the MRI tube 2.

A complete ring comprising the LSO crystal arrays 4 and the APD photodiode arrays 5, of which the AMPs 6 are seated outside the second field of view, is respectively advantageously arranged at the outer edges of the second field of view in the z-direction, in order to raise the sensitivity at the edge.

FIG. 4 shows an arrangement of PET detection units 3 in a device for superposed MRI and PET imaging in accordance with the third example embodiment of the present invention.

The third example embodiment is modified with regard to the second exemplary embodiment to the effect that more PET detection units 3 are omitted at the center of the second field of view in the z-direction than at the edge thereof in the z-direction.

For optimization, the system should be simulated, and an optimized occupancy should then be defined, preferably with the aid of a modulation transfer function (MTF).

The first to third example embodiments have the following advantages: firstly, costs are spared on the basis of the reduced number of PET detection units 3.

In addition, radial space is spared in the gantry, since the AMP 6 is arranged next to the associated LSO crystal arrays 4 and APD photodiode arrays 5. This also leads to a less expensive MRI system integration.

A further advantage is the fact that the dimensions of the entire system are prescribed until further notice by the magnet of the MRI tube 2. The requirements of keeping a PET gantry as short and small as possible for reasons of design and claustrophobia are thereby eliminated in any case.

The invention is not restricted by the disclosed example embodiments, but there is a possibility of modifications and equivalent embodiments within the scope of the invention that is defined by the claims.

Example embodiments being thus described, it will be obvious that the same may be varied in many ways. Such variations are not to be regarded as a departure from the spirit and scope of the present invention, and all such modifications as would be obvious to one skilled in the art are intended to be included within the scope of the following claims.

What is claimed is:

1. A device for superposed magnetic resonance tomography and positron emission tomography imaging, comprising:
   a magnetic resonance tomography tube that defines a first field of view along its longitudinal direction;
   a multiplicity of positron emission tomography detection units arranged opposite one another in pairs about the longitudinal direction, the multiplicity of positron emission tomography detection units defining a second field of view along the longitudinal direction, wherein
   the positron emission tomography detection units respectively include an avalanche photodiode array with an upstream lutetium oxyorthosilicate crystal array and an electrical amplifier circuit,
   a spacing at least corresponding to an avalanche photodiode array is present between two neighboring avalanche photodiode arrays, and
   for each positron emission tomography detection unit, the electrical amplifier circuit is arranged in a plane, parallel to the longitudinal direction, next to at least one of the lutetium oxyorthosilicate crystal array and the avalanche photodiode array, wherein the portion of the total area of said plane which is occupied by the lutetium oxyorthosilicate crystals defines an arrangement density of the positron emission tomography detection units in said plane, and
   said arrangement density of the positron emission tomography detection units being provided along the longitudinal direction such that the second field of view is substantially equal to the first field of view.

2. The device as claimed in claim 1, wherein the positron emission tomography detection units are respectively oriented at the end of the second field of view in the longitudinal direction such that at least one of the lutetium oxyorthosilicate crystal array and the avalanche photodiode array is oriented toward the middle of the magnetic resonance tomography tube, and the electrical amplifier circuit is oriented toward the edge of the magnetic resonance tomography tube.

3. The device as claimed in claim 1, wherein the arrangement density of the positron emission tomography detection units along the longitudinal direction becomes relatively larger from the middle of the second field of view toward the edge thereof.

* * * * *